United States Patent
Nakae et al.

(10) Patent No.: US 9,624,177 B2
(45) Date of Patent: Apr. 18, 2017

(54) METHOD FOR PRODUCING PYRAZOLE COMPOUND

(71) Applicant: SUMITOMO CHEMICAL COMPANY, LIMITED, Tokyo (JP)

(72) Inventors: Yasuyuki Nakae, Takarazuka-shi (JP); Takashi Miyamoto, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/113,494

(22) PCT Filed: Feb. 16, 2015

(86) PCT No.: PCT/JP2015/054899
§ 371 (c)(1),
(2) Date: Jul. 22, 2016

(87) PCT Pub. No.: WO2015/129591
PCT Pub. Date: Sep. 3, 2015

(65) Prior Publication Data
US 2017/0008853 A1    Jan. 12, 2017

(30) Foreign Application Priority Data

Feb. 28, 2014 (JP) .................................. 2014-038519

(51) Int. Cl.
*C07D 231/22* (2006.01)

(52) U.S. Cl.
CPC .................................. *C07D 231/22* (2013.01)

(58) Field of Classification Search
None
See application file for complete search history.

(56) References Cited

U.S. PATENT DOCUMENTS

| 5,807,863 | A | 9/1998 | Eberle et al. |
| 6,040,458 | A | 3/2000 | Vogelbacher et al. |

FOREIGN PATENT DOCUMENTS

| CN | 102485743 A | 6/2012 |
| GB | 1 377 596 | 12/1974 |

OTHER PUBLICATIONS

Azarifar et al., "Microwave-Promoted Oxidation of 1,3,5-Trisubstituted 4,5- Dihydro-1H-pyrazoles by In-Situ generation of $NO^+$ and $NO_2+$ respectively from Sodium Nitrite and Sodium Nitrate in Acetic Acid", Journal of Heterocyclic Chemistry, vol. 45, Mar.-Apr. 2008, pp. 563-565.
International Search Report (PCT/ISA/210) issued in PCT/JP2015/054899, mailed on May 26, 2015.
International Preliminary Report on Patentability and English translation of the Written Opinion of the International Searching Authority (forms PCT/IB/373 and PCT/ISA/237), issued Sep. 6, 2016, for International Application No. PCT/JP2015/054899.

*Primary Examiner* — Kamal Saeed
(74) *Attorney, Agent, or Firm* — Birch, Stewart, Kolasch & Birch, LLP

(57) ABSTRACT

A method for producing a pyrazole compound represented by formula (1):

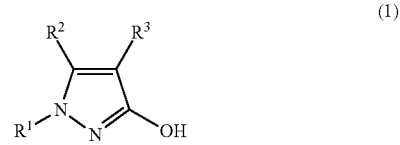

(1)

(wherein $R^1$ represents an optionally substituted $C_{1-12}$ alkyl group, an optionally substituted $C_{3-12}$ cycloalkyl group, an optionally substituted $C_{6-16}$ aryl group, or an optionally substituted pyridyl group, $R^2$ and $R^3$ each independently represent a hydrogen atom, a halogen atom, a $C_{1-3}$ alkyl group, or a $C_{1-3}$ haloalkyl group), said method including a step in which a pyrazolidine compound represented by formula (2):

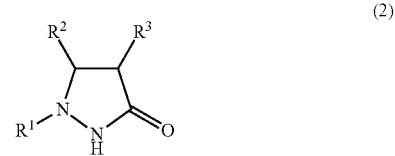

(2)

(wherein $R^1$, $R^2$, and $R^3$ are as defined above)
is reacted with a nitrite in the presence of an acid, allows a pyrazole compound to be produced industrially.

8 Claims, No Drawings

METHOD FOR PRODUCING PYRAZOLE COMPOUND

TECHNICAL FIELD

The present invention relates to a method for producing a pyrazole compound.

BACKGROUND ART

Pyrazole compounds having a hydroxyl group at the 3-position, such as 1-(4-chlorophenyl)-3-hydroxypyrazole, are useful as intermediates in the production of pharmaceuticals, etc., and an industrial production method therefore has been desired.

U.S. Pat. No. 6,040,458 discloses a production method including oxidizing 1-(4-chlorophenyl)pyrazolidin-3-one in water using oxygen in the presence of a base and a metal salt such as cobalt acetate.

SUMMARY OF THE INVENTION

The present invention includes the following invention.
[1] A method for producing a pyrazole compound represented by formula (1):

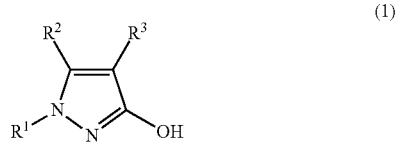

(1)

(wherein $R^1$ represents an optionally substituted $C_{1-12}$ alkyl group, an optionally substituted $C_{3-12}$ cycloalkyl group, an optionally substituted $C_{6-16}$ aryl group, or an optionally substituted pyridyl group, $R^2$ and $R^3$ each independently represent a hydrogen atom, a halogen atom, a $C_{1-3}$ alkyl group, or a $C_{1-3}$ haloalkyl group), comprising a step of allowing a pyrazolidine compound represented by formula (2):

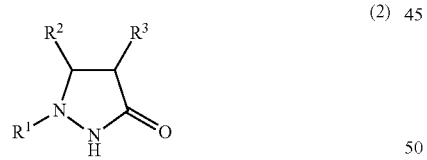

(2)

(wherein $R^1$, $R^2$, and $R^3$ are as defined above) to react with a nitrite in the presence of an acid.
[2] The method according to [1], further comprising a step of allowing a hydrazine compound represented by formula (3):

(3)

(wherein $R^1$ represents an optionally substituted $C_{1-12}$ alkyl group, an optionally substituted $C_{3-12}$ cycloalkyl group, an optionally substituted $C_{6-16}$ aryl group, or an optionally substituted pyridyl group)

to react with a compound represented by formula (4):

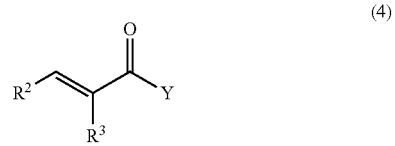

(4)

(wherein Y represents a $C_{1-4}$ alkoxy group, and $R^2$ and $R^3$ each independently represent a hydrogen atom, a halogen atom, a $C_{1-3}$ alkyl group, or a $C_{1-3}$ haloalkyl group)
in the presence of a base, thereby giving the pyrazolidine compound represented by formula (2).

MODE FOR CARRYING OUT THE INVENTION

The present invention is a method for producing a pyrazole compound represented by formula (1) (hereinafter may be referred to as pyrazole (1)):

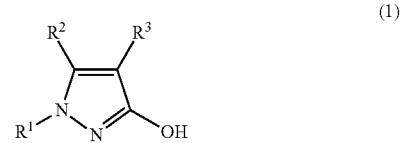

(1)

(wherein $R^1$ represents an optionally substituted $C_{1-12}$ alkyl group, an optionally substituted $C_{3-12}$ cycloalkyl group, an optionally substituted $C_{6-16}$ aryl group, or an optionally substituted pyridyl group, $R^2$ and $R^3$ each independently represent a hydrogen atom, a halogen atom, a $C_{1-3}$ alkyl group, or a $C_{1-3}$ haloalkyl group), comprising a step of allowing a pyrazolidine compound represented by formula (2) (hereinafter may be referred to as pyrazolidine (2)):

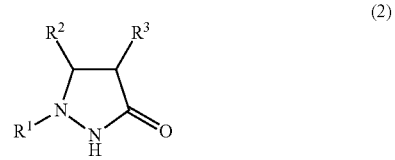

(2)

(wherein $R^1$, $R^2$, and $R^3$ are as defined above)
to react with a nitrite in the presence of an acid.

Examples of the $C_{1-12}$ alkyl group include a methyl group, an ethyl group, a propyl group, an isopropyl group, a butyl group, an isobutyl group, a tert-butyl group, a pentyl group, a hexyl group, an octyl group, a decyl group, and a dodecyl group. A $C_{1-6}$ alkyl group is preferable, and a $C_{1-4}$ alkyl group is more preferable.

Such an alkyl group is optionally substituted with at least one substituent, and the substituent is a substituent inert to the reaction. Specifically, examples thereof include a halogen atom such as a fluorine atom, a chlorine atom, and a bromine atom; a $C_{1-6}$ alkoxy group such as a methoxy group, an ethoxy group, a propoxy group, an isopropoxy group, a butoxy group, a tert-butoxy group, and a hexyloxy group; a $C_{1-6}$ haloalkoxy group such as a trifluoromethoxy group and a pentafluoroethoxy group; a nitro group; and a cyano group. Specific examples of substituted $C_{1-12}$ alkyl groups include a trifluoromethyl group.

Examples of the $C_{3-12}$ cycloalkyl group include a cyclopentyl group, a cyclohexyl group, and a cyclooctyl group, and a $C_{3-8}$ cycloalkyl group is preferable. Such a cycloalkyl group is optionally substituted with at least one substituent, and the substituent is a substituent inert to the reaction. Specifically, examples thereof include the above halogen atom; the above $C_{1-6}$ alkoxy group; the above $C_{1-6}$ haloalkoxy group; a nitro group; and a cyano group. Specific examples of the substituted $C_{3-12}$ cycloalkyl group include a 4-fluorocyclohexyl group.

Examples of the $C_{6-16}$ aryl group include a phenyl group, a 2-methylphenyl group, a 3-methylphenyl group, a 4-methylphenyl group, a 2-ethylphenyl group, a 4-ethylphenyl group, and a naphthalen-2-yl group, and a $C_{6-12}$ aryl group is preferable. Such an aryl group is optionally substituted with at least one substituent, and the substituent is a substituent inert to the reaction. Specifically, examples thereof include the above halogen atom; the above $C_{1-6}$ alkoxy group; a $C_{1-6}$ haloalkyl group such as a chloromethyl group, a fluoromethyl group, a trifluoromethyl group, a pentafluoroethyl group, and a nonafluorobutyl group; the above $C_{1-6}$ haloalkoxy group; a nitro group; and a cyano group. Specific examples of the substituted $C_{6-16}$ aryl group include a 2-fluorophenyl group, a 3-fluorophenyl group, a 4-fluorophenyl group, a pentafluorophenyl group, a 2-chlorophenyl group, a 3-chlorophenyl group, a 4-chlorophenyl group, a 2-bromophenyl group, a 3-bromophenyl group, a 4-bromophenyl group, a 3-fluoro-4-methoxyphenyl group, a 2-methoxyphenyl group, a 3-methoxyphenyl group, a 4-methoxyphenyl group, a 4-ethoxyphenyl group, a 2-isopropoxy phenyl group, a 2-fluoro-4-methylphenyl group, a 3-fluoro-4-methylphenyl group, a 4-chloro-3-fluorophenyl group, a 4-(trifluoromethyl)phenyl group, a 4-(trifluoromethoxy)phenyl group, a 3-chloro-2-methoxyphenyl group, a 4-chloro-2-methoxyphenyl group, a 5-chloro-2-methoxyphenyl group, a 4-nitrophenyl group, and a 4-cyanophenyl group.

The pyridyl group is optionally substituted with at least one substituent, and the substituent is a substituent inert to the reaction. Specifically, examples thereof include a $C_{1-6}$ alkyl group such as a methyl group, an ethyl group, a propyl group, an isopropyl group, a butyl group, an isobutyl group, a tert-butyl group, a pentyl group, and a hexyl group; the above halogen atom; the above $C_{1-6}$ alkoxy group; a $C_{1-6}$ haloalkyl group such as a chloromethyl group, a fluoromethyl group, a trifluoromethyl group, a pentafluoroethyl group, and a nonafluorobutyl group; the above $C_{1-6}$ haloalkoxy group; a nitro group; and a cyano group. Specific examples of the optionally substituted pyridyl group include a pyridin-2-yl group, a pyridin-3-yl group, a pyridin-4-yl group, a 2-methoxypyridin-3-yl group, a 6-chloropyridin-3-yl group, a 6-bromo-2-methoxypyridin-3-yl group, a 6-chloro-2-methoxypyridin-3-yl group, a 2,6-dimethoxypyridin-3-yl group, a 5-chloro-2-methoxypyridin-3-yl group, a 6-methyl-2-methoxypyridin-3-yl group, a 6-cyano-2-methoxypyridin-3-yl group, a 6-(trifluoromethyl)-2-methoxypyridin-3-yl group, a 5-methylpyridin-2-yl group, a 6-methylpyridin-2-yl group, and a 5-(trifluoromethyl) pyridin-2-yl group.

$R^1$ is preferably an optionally substituted $C_{6-16}$ aryl group or an optionally substituted pyridyl group, and more preferably a $C_{6-16}$ aryl group optionally substituted with at least one substituent selected from the following group P or a pyridyl group optionally substituted with at least one substituent selected from the following group Q.

Group P: a halogen atom, a $C_{1-6}$ alkoxy group, a $C_{1-6}$ haloalkyl group, a $C_{1-6}$ haloalkoxy group, a nitro group, and a cyano group Group Q: a $C_{1-6}$ alkyl group, a halogen atom, a $C_{1-6}$ alkoxy group, a $C_{1-6}$ haloalkyl group, a $C_{1-6}$ haloalkoxy group, a nitro group, and a cyano group Examples of the halogen atom represented by $R^2$ and $R^3$ include a fluorine atom, a chlorine atom, and a bromine atom, examples of the $C_{1-3}$ alkyl group include a methyl group, an ethyl group, a propyl group, and an isopropyl group, and examples of the $C_{1-3}$ haloalkyl group include a trifluoromethyl group and a pentafluoroethyl group.

It is preferable that $R^2$ and $R^3$ are each independently a hydrogen atom, a halogen atom, or a $C_{1-3}$ alkyl group, it is more preferable that one is a hydrogen atom, while the other is a hydrogen atom, a halogen atom, or a $C_{1-3}$ alkyl group, and it is particularly preferable that both are hydrogen atoms.

Specific examples of pyrazolidine (2) include 1-phenylpyrazolidin-3-one, 1-(2-fluorophenyl)pyrazolidin-3-one, 1-(3-fluorophenyl)pyrazolidin-3-one, 1-(4-fluorophenyl)pyrazolidin-3-one, 1-(pentafluorophenyl)pyrazolidin-3-one, 1-(2-chlorophenyl)pyrazolidin-3-one, 1-(3-chlorophenyl)pyrazolidin-3-one, 1-(4-chlorophenyl)pyrazolidin-3-one, 1-(2-bromophenyl)pyrazolidin-3-one, 1-(3-bromophenyl)pyrazolidin-3-one, 1-(4-bromophenyl)pyrazolidin-3-one, 1-(3-fluoro-4-methoxypheny)pyrazolidin-3-one, 1-(2-methylphenyl)pyrazolidin-3-one, 1-(3-methylphenyl)pyrazolidin-3-one, 1-(4-methylphenyl)pyrazolidin-3-one, 1-(2-ethylphenyl)pyrazolidin-3-one, 1-(4-ethylphenyl)pyrazolidin-3-one, 1-(2-methoxypheny)pyrazolidin-3-one, 1-(3-methoxypheny)pyrazolidin-3-one, 1-(4-methoxypheny)pyrazolidin-3-one, 1-(4-ethoxyphenyl)pyrazolidin-3-one, 1-(2-isopropyloxyphenyl)pyrazolidin-3-one, 1-(2-fluoro-4-methylphenyl)pyrazolidin-3-one, 1-(3-fluoro-4-methylphenyl)pyrazolidin-3-one, 1-(4-chloro-3-fluorophenyl)pyrazolidin-3-one, 1-[4-(trifluoromethyl)phenyl]pyrazolidin-3-one, 1-[4-(trifluoromethoxy)phenyl]pyrazolidin-3-one, 1-(3-chloro-2-methoxypheny)pyrazolidin-3-one, 1-(4-chloro-2-methoxypheny)pyrazolidin-3-one, 1-(5-chloro-2-methoxypheny)pyrazolidin-3-one, 1-(4-nitrophenyl)pyrazolidin-3-one, 1-(4-cyanophenyl)pyrazolidin-3-one, 1-(naphthalen-2-yl)pyrazolidin-3-one, tert-butylpyrazolidin-3-one, cyclohexylpyrazolidin-3-one, 1-(pyridin-3-yl)pyrazolidin-3-one, 1-(2-methoxypyridin-3-yl)pyrazolidin-3-one, 1-(6-chloropyridin-3-yl)pyrazolidin-3-one, 1-(6-bromo-2-methoxypyridin-3-yl)pyrazolidin-3-one, 1-(6-chloro-2-methoxypyridin-3-yl)pyrazolidin-3-one, 1-(2,6-dimethoxypyridin-3-yl)pyrazolidin-3-one, 1-(5-chloro-2-methoxypyridin-3-yl)pyrazolidin-3-one, 1-(6-methyl-2-methoxypyridin-3-yl)pyrazolidin-3-one, 1-(6-cyano-2-methoxypyridin-3-yl)pyrazolidin-3-one, 1-[6-(trifluoromethyl)-2-methoxypyridin-3-yl]pyrazolidin-3-one, 1-(pyridin-2-yl)pyrazolidin-3-one, 1-(5-methylpyridin-2-yl)pyrazolidin-3-one, 1-(6-methylpyridin-2-yl)pyrazolidin-3-one, 1-[5-(trifluoromethyl)pyridin-2-yl]pyrazolidin-3-one, 1-(pyridin-4-yl)pyrazolidin-3-one, 1-(4-chlorophenyl)-4-methylpyrazolidin-3-one, 1-(4-chlorophenyl)-5-methylpyrazolidin-3-one, 4-bromo-1-(4-chlorophenyl)pyrazolidin-3-one, and 1-(2-methoxypyridin-3-yl)-5-methylpyrazolidin-3-one.

Examples of the nitrite include an alkali metal nitrite such as sodium nitrite and potassium nitrite, an alkaline earth metal nitrite such as calcium nitrite, and silver nitrite. An alkali metal nitrite is preferable, and sodium nitrite is more preferable. The amount of the nitrite to be used is usually 1 mol to 20 mol, preferably 2 mol to 10 mol, per mole of pyrazolidine (2). The nitrite may also be used in the form of a solution such as an aqueous solution.

Examples of the acid include a hydrogen halide such as hydrogen chloride and hydrogen bromide, sulfuric acid, phosphoric acid, and an alkanesulfonic acid such as methanesulfonic acid. A hydrogen halide is preferable, and hydrogen chloride is more preferable. Such an acid may also be used in the form of a solution such as an aqueous solution, like hydrochloric acid. The amount of the acid to be used is usually 1 mol to 10 mol, preferably 1 mol to 3 mol, per mole of the nitrite.

The reaction is usually carried out in a solvent. Examples of the solvent include water and a mixed solvent of water and an organic solvent. Examples of the organic solvent include an aromatic hydrocarbon solvent such as toluene and xylene; a halogenated aromatic hydrocarbon solvent such as chlorobenzene and 1,2-dichlorobenzene; a saturated hydrocarbon solvent such as hexane, cyclohexane, and heptane; a halogenated hydrocarbon solvent such as dichloromethane, chloroform, and 1,2-dichloroethane; a nitrile solvent such as acetonitrile, butyronitrile, and benzonitrile; an aprotic amide solvent such as N,N-dimethylformamide, N-methylpyrrolidone, and N,N-dimethylimidazolidinone; an ether solvent such as diethyl ether, diisopropyl ether, methyl tert-butyl ether, and tetrahydrofuran; and a carboxylate solvent such as propyl acetate and butyl acetate. It is also possible to use a combination of two or more kinds of organic solvents. The solvent is preferably water, a mixed solvent of an aromatic hydrocarbon solvent and water, or a mixed solvent of a nitrile solvent and water. The amount of the solvent to be used is usually 0.5 parts by mass to 50 parts by mass, preferably 1 part by mass to 20 parts by mass, per 1 part by mass of pyrazolidine (2). In a mixed solvent of an organic solvent and water, the proportion of water relative to the organic solvent is not limited.

The reaction is usually carried out by mixing pyrazolidine (2) and the nitrite in the presence of an acid, and the order of mixing is not limited. The reaction is preferably carried out by a method in which the nitrite is added to a mixture of pyrazolidine (2) and an acid, or a method in which an acid is added to a mixture of pyrazolidine (2) and the nitrite.

The reaction temperature is usually 0° C. to 25° C., preferably 0° C. to 10° C. The reaction time is usually 1 hour to 50 hours.

After the completion of the reaction, for example, the obtained reaction mixture is filtered, whereby pyrazole (1) can be isolated. It is also possible that the reaction mixture is treated with a reducing agent such as a sulfite to decompose the unreacted nitrite, and then pyrazole (1) is isolated. The isolated pyrazole (1) may be further purified by an ordinary purification technique such as chromatography or recrystallization.

Specific examples of pyrazole (1) include 1-phenyl-1H-pyrazol-3-ol, 1-(2-fluorophenyl)-1H-pyrazol-3-ol, 1-(3-fluorophenyl)-1H-pyrazol-3-ol, 1-(4-fluorophenyl)-1H-pyrazol-3-ol, 1-(pentafluorophenyl)-1H-pyrazol-3-ol, 1-(2-chlorophenyl)-1H-pyrazol-3-ol, 1-(3-chlorophenyl)-1H-pyrazol-3-ol, 1-(4-chlorophenyl)-1H-pyrazol-3-ol, 1-(2-bromophenyl)-1H-pyrazol-3-ol, 1-(3-bromophenyl)-1H-pyrazol-3-ol, 1-(4-bromophenyl)-1H-pyrazol-3-ol, 1-(3-fluoro-4-methoxypheny)-1H-pyrazol-3-ol, 1-(2-methylphenyl)-1H-pyrazol-3-ol, 1-(3-methylphenyl)-1H-pyrazol-3-ol, 1-(4-methylphenyl)-1H-pyrazol-3-ol, 1-(2-ethylphenyl)-1H-pyrazol-3-ol, 1-(4-ethylphenyl)-1H-pyrazol-3-ol, 1-(2-methoxypheny)-1H-pyrazol-3-ol, 1-(3-methoxyphenyl)-1H-pyrazol-3-ol, 1-(4-methoxyphenyl)-1H-pyrazol-3-ol, 1-(2-ethoxyphenyl)-1H-pyrazol-3-ol, 1-(2-isopropyloxyphenyl)-1H-pyrazol-3-ol, 1-(2-fluoro-4-methylphenyl)-1H-pyrazol-3-ol, 1-(3-fluoro-4-methylphenyl)-1H-pyrazol-3-ol, 1-(4-chloro-3-fluorophenyl)-1H-pyrazol-3-ol, 1-[4-(trifluoromethyl)phenyl]-1H-pyrazol-3-ol, 1-[4-(trifluoromethoxy)phenyl]-1H-pyrazol-3-ol, 1-(3-chloro-2-methoxyphenyl)-1H-pyrazol-3-ol, 1-(4-chloro-2-methoxyphenyl)-1H-pyrazol-3-ol, 1-(5-chloro-2-methoxyphenyl)-1H-pyrazol-3-ol, 1-(4-nitrophenyl)-1H-pyrazol-3-ol, 1-(4-cyanophenyl)-1H-pyrazol-3-ol, 1-(naphthalen-2-yl)-1H-pyrazol-3-ol, 1-tert-butyl-1H-pyrazol-3-ol, 1-cyclohexyl-1H-pyrazol-3-ol, 1-(pyridin-3-yl)-1H-pyrazol-3-ol, 1-(2-methoxypyridin-3-yl)-1H-pyrazol-3-ol, 1-(6-chloropyridin-3-yl)-1H-pyrazol-3-ol, 1-(6-bromo-2-methoxypyridin-3-yl)-1H-pyrazol-3-ol, 1-(6-chloro-2-methoxypyridin-3-yl)-1H-pyrazol-3-ol, 1-(2,6-dimethoxypyridin-3-yl)-1H-pyrazol-3-ol, 1-(5-chloro-2-methoxypyridin-3-yl)-1H-pyrazol-3-ol, 1-(6-methyl-2-methoxypyridin-3-yl)-1H-pyrazol-3-ol, 1-(6-cyano-2-methoxypyridin-3-yl)-1H-pyrazol-3-ol, 1-[6-(trifluoromethyl)-2-methoxypyridin-3-yl]-1H-pyrazol-3-ol, 1-(pyridin-2-yl)-1H-pyrazol-3-ol, 1-(5-methylpyridin-2-yl)-1H-pyrazol-3-ol, 1-(6-methylpyridin-2-yl)-1H-pyrazol-3-ol, 1-[5-(trifluoromethyl)pyridin-2-yl]-1H-pyrazol-3-ol, 1-(pyridin-4-yl)-1H-pyrazol-3-ol, 1-(4-chlorophenyl)-4-methyl-1H-pyrazol-3-ol, 1-(4-chlorophenyl)-5-methyl-1H-pyrazol-3-ol, 4-bromo-1-(4-chlorophenyl)-1H-pyrazol-3-ol, and 1-(2-methoxypyridin-3-yl)-5-methyl-1H-pyrazol-3-ol.

Pyrazolidine (2) can be produced by allowing a hydrazine compound represented by formula (3) (hereinafter may be referred to as hydrazine (3)):

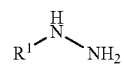

(wherein $R^1$ is as defined above)
to react with a compound represented by formula (4) (hereinafter may be referred to as compound (4)):

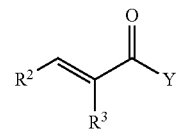

(wherein Y represents a $C_{1-4}$ alkoxy group, and $R^2$ and $R^3$ are as defined above)
in the presence of a base.

Specific examples of hydrazine (3) include phenylhydrazine, 2-fluorophenylhydrazine, 3-fluorophenylhydrazine, 4-fluorophenylhydrazine, pentafluorophenylhydrazine, 2-chlorophenylhydrazine, 3-chlorophenylhydrazine, 4-chlorophenylhydrazine, 2-bromophenylhydrazine, 3-bromophenylhydrazine, 4-bromophenylhydrazine, 3-fluoro-4-methoxyphenylhydrazine, 2-methylphenylhydrazine, 3-methylphenylhydrazine, 4-methylphenylhydrazine, 2-ethylphenylhydrazine, 4-ethylphenylhydrazine, 2-methoxyphenylhydrazine, 3-methoxyphenylhydrazine, 4-methoxyphenylhydrazine, 4-ethoxyphenylhydrazine, 2-isopropyloxyphenylhydrazine, 2-fluoro-4-methylphenylhydrazine, 3-fluoro-4-methylphenylhydrazine, 4-chloro-3-fluorophenylhydrazine, 4-(trifluoromethyl)phenylhydrazine, 4-(trifluoromethoxy)phenylhydrazine, 3-chloro-2-methoxyphenylhydrazine, 4-chloro-2-methoxyphenylhydrazine, 5-chloro-2-methoxyphenylhydrazine, 4-nitrophenylhydrazine, 4-cyanophenylhydrazine, naphthalen-2-ylhydrazine, tert-butylhydrazine, cyclohexylhydrazine, 3-hydrazinopyridine, 3-hydrazino-2-methoxypyridine, 6-chloro-3-hydrazinopyridine, 6-bromo-3-hydrazino-2-methoxypyridine, 6-chloro-3-hydrazino-2-methoxypyridine, 2,6-dimethoxy-3-hydrazinopyridine, 5-chloro-3-hydrazino-2-methoxypyridine, 6-methyl-3-hydrazino-2-methoxypyridine, 6-cyano-3-hydrazino-2-methoxypyridine, 3-hydrazino-6-(trifluoromethyl)-2-methoxypyridine, 2-hydrazinopyridine, 2-hydrazino-5-methylpyridine, 2-hydrazino-6-methylpyridine, 2-hydrazino-5-(trifluoromethyl)pyridine, and 4-hydrazinopyridine. Hydrazine (3) may be in the form of an acid addition salt such as a hydrochloride, a sulfate, a methanesulfonate, or a p-toluenesulfonate.

Examples of the $C_{1-4}$ alkoxy group represented by Y in formula (4) include a methoxy group, an ethoxy group, a propoxy group, an isopropoxy group, a butoxy group, an isobutoxy group, and a tert-butoxy group.

Examples of compound (4) include methyl acrylate, ethyl acrylate, propyl acrylate, butyl acrylate, ethyl methacrylate, ethyl crotonate, 4,4,4-trifluoroethyl crotonate, and 2-bromoethyl acrylate.

The amount of compound (4) to be used is usually 1 mol to 10 mol, preferably 3 mol to 5 mol, per mole of hydrazine (3).

Examples of the base include an alkali metal hydroxide such as sodium hydroxide and potassium hydroxide; and an alkali metal alkoxide such as sodium methoxide, sodium ethoxide, and potassium tert-butoxide. An alkali metal alkoxide is preferable, and sodium methoxide is more preferable. The amount of the base to be used is usually 1 mol to 5 mol, preferably 2 mol to 3 mol, per mole of hydrazine (3). In the case where hydrazine (3) is used in the form of an acid addition salt, usually, an amount of base sufficient for neutralizing the acid of the acid addition salt is further used.

The reaction of hydrazine (3) and compound (4) is usually carried out in a solvent. Examples of the solvent include an aromatic hydrocarbon solvent such as toluene and xylene; a halogenated aromatic hydrocarbon solvent such as chlorobenzene and 1,2-dichlorobenzene; a saturated hydrocarbon solvent such as hexane, cyclohexane, and heptane; a halogenated aliphatic hydrocarbon solvent such as dichloromethane, chloroform, and 1,2-dichloroethane; a nitrile solvent such as acetonitrile, butyronitrile, and benzonitrile; an aprotic amide solvent such as N,N-dimethylformamide, N-methylpyrrolidone, and N,N-dimethylimidazolidinone; an ether solvent such as diethyl ether, diisopropyl ether, methyl tert-butyl ether, and tetrahydrofuran; a carboxylate solvent such as propyl acetate and butyl acetate; and an alcohol solvent such as methanol, ethanol, and 2-propanol. It is also possible to use a combination of two or more kinds of solvents. The solvent is preferably an aromatic hydrocarbon solvent, a halogenated aromatic hydrocarbon solvent, a saturated hydrocarbon solvent, or a mixed solvent of a halogenated aliphatic hydrocarbon solvent and an alcohol solvent. Among them, a mixed solvent of a solvent having a higher boiling point than alcohol solvents and an alcohol solvent is more preferable. The amount of the solvent to be used is usually 0.5 parts by mass to 20 parts by mass per part by mass of hydrazine (3).

The reaction of hydrazine (3) and compound (4) is usually carried out by mixing hydrazine (3), compound (4), and a base. The order of mixing is not limited, and the reaction is carried out, for example, by adding compound (4) to a mixture of hydrazine (3) and a base.

The reaction temperature is usually 20° C. to 150° C., preferably 40° C. to 80° C. The reaction time is usually 1 hour to 50 hours.

After the completion of the reaction, for example, water is added to the obtained reaction mixture together with an organic solvent as necessary, and then concentrated, whereby pyrazolidine (2) can be isolated. In addition, it is also possible that after adding water to the reaction mixture, the obtained liquid is separated into an organic layer and an aqueous layer, and the aqueous layer is concentrated to isolate pyrazolidine (2). The amount of water to be added to the reaction mixture is usually 1 part by mass to 10 parts by mass, preferably 1 part by mass to 4 parts by mass, per part by mass of hydrazine (3).

The obtained pyrazolidine (2) is preferably washed with an aqueous solution of an acid such as hydrochloric acid or sulfuric acid. Pyrazolidine (2) may be further purified by an ordinary purification technique such as chromatography or recrystallization. In addition, the obtained reaction mixture maybe directly, or after concentration, used for the reaction between pyrazolidine (2) and a nitrite described above. In the case where the reaction mixture contains a solvent that may react with a nitrite, it is preferable that the solvent is removed from the reaction mixture by any means such as concentration, and the resulting concentrate is used for the reaction of pyrazolidine (2) and a nitrite described above.

EXAMPLES

Hereinafter, the present invention will be described in further detail with reference to examples. The contents were calculated based on the results of high-performance liquid chromatography (HPLC) analysis.

Reference Example 4.01 g of 4-chlorophenylhydrazine hydrochloride and 12.02 g of xylene were mixed, and 13.33 g of a 28 wt % sodium methylate/methanol solution was added to the obtained mixture. The obtained mixture was heated to 70° C., and then 10.0 mL of ethyl acrylate was added dropwise. The obtained mixture was stirred at the same temperature for 2 hours. 24.0 g of heptane was added to the obtained reaction mixture and filtered. The obtained solid was washed with heptane, water, 10 wt % hydrochloric acid, and then water, followed by drying to give 3.40 g of 1-(4-chlorophenyl)pyrazolidin-3-one (content: 96.2%). Yield: 77.0%.

Example 1

Under a nitrogen atmosphere, 0.80 g of 1-(4-chlorophenyl)pyrazolidin-3-one, 1.03 g of concentrated hydrochloric acid, and 3.0 g of water were mixed and ice-cooled. To this mixture, an aqueous solution prepared by dissolving 565.8 mg of sodium nitrite in 1.14 g of water was added dropwise. The obtained mixture was stirred with ice-cooling for 3 hours, water was added, and then the solid was collected by filtration. The obtained solid was washed with water and then hexane, followed by drying to give 0.80 g of 4-chlorophenyl-1H-pyrazol-3-ol (content: 83.3 wt %). Yield: 84.1%.

Example 2

Under a nitrogen atmosphere, 103 mg of 1-(4-chlorophenyl)pyrazolidin-3-one, 38.5 mg of sodium nitrite, and 1.0 mL of acetonitrile were mixed and ice-cooled. 0.5 mL of 10 wt % hydrochloric acid was added to this mixture and stirred with ice-cooling for 2.5 hours, and then a small amount of sodium nitrite was added and stirred for 0.5 hours. Water and an aqueous sodium sulfite solution were added to the obtained reaction mixture, and then the solid was collected by filtration. The obtained solid was washed with water, methyl tert-butyl ether, and then hexane, followed by drying to give 86.5 mg of 4-chlorophenyl-1H-pyrazol-3-ol.

Example 3

Under a nitrogen atmosphere, 302 mg of 1-(4-chlorophenyl)pyrazolidin-3-one, 127 mg of sodium nitrite, and 1.0 mL of xylene were mixed and ice-cooled. 1.0 mL of 10 wt % hydrochloric acid was added to this mixture and stirred with ice-cooling for 3 hours, and then a small amount of sodium nitrite was added and stirred for 0.5 hours. Water, an aqueous sodium sulfite solution, and methyl tert-butyl ether were added to the obtained reaction mixture, and then the solid was collected by filtration. The obtained solid was dried to give 220 mg of 4-chlorophenyl-1H-pyrazol-3-ol.

Example 4

30.14 g of 4-chlorophenylhydrazine hydrochloride and 100.1 g of toluene were mixed. Subsequently, under a nitrogen atmosphere, a 28 wt % sodium methoxide/methanol solution was added, and further 20.2 g of toluene was added, followed by heating to 50° C. A mixed solution of 50.70 g of ethyl acrylate and 30.3 g of toluene was added dropwise to this mixture, stirred at 50° C. for 1 hour, and further stirred at 70° C. for 2 hours to give a reaction mixture containing 1-(4-chlorophenyl)pyrazolidin-3-one. 30.3 g of water was added to the reaction mixture and then concentrated. 58.0 g of concentrated hydrochloric acid was added to the concentrated residue, and an aqueous solution prepared by mixing 23.12 g of sodium nitrite and 46.3 g of water was added dropwise to this mixture at about 5° C. The obtained mixture was stirred at the same temperature for 1.5 hours and then filtered. The obtained solid was washed with toluene, water, a mixed liquid of heptane and water, and then heptane, followed by drying to give 26.7 g of 4-chlorophenyl-1H-pyrazol-3-ol (content: 99.0 wt %). Yield: 80.7% (based on 4-chlorophenylhydrazine hydrochloride).

The filtrate obtained by filtering the mixture contained 1.81 g of 4-chlorophenyl-1H-pyrazol-3-ol.

Example 5

4.01 g of 4-chlorophenylhydrazine hydrochloride, 16.1 g of toluene, and 14.4 g of a 28 wt % sodium methoxide/methanol solution were mixed and heated to 70° C. under a nitrogen atmosphere. Subsequently, a mixed solution of 6.76 g of ethyl acrylate and 4.0 g of toluene was added dropwise. The obtained mixture was stirred at 70° C. for 2 hours to give a reaction mixture containing 1-(4-chlorophenyl)pyrazolidin-3-one. 8.0 g of water was added to the reaction mixture and then concentrated. An aqueous solution prepared by mixing 3.08 g of sodium nitrite and 6.1 g of water was added to the concentrated residue with ice-cooling, and further 7.7 g of concentrated hydrochloric acid was added. The obtained mixture was stirred with ice-cooling for 1.5 hours. The obtained reaction mixture was filtered, the obtained solid was washed with toluene, water, hexane, and then water, and the obtained solid was dried to give 3.75 g of 4-chlorophenyl-1H-pyrazol-3-ol (content: 97.9 wt %). Yield: 84.2% (based on 4-chlorophenylhydrazine hydrochloride).

The filtrate obtained by filtering the reaction mixture contained 0.26 g of 4-chlorophenyl-1H-pyrazol-3-ol.

Example 6

4.00 g of 4-chlorophenylhydrazine hydrochloride, 12.2 g of heptane, and 17.4 g of a 28 wt % sodium methoxide/methanol solution were mixed and heated to 70° C. under a nitrogen atmosphere. Subsequently, a mixed solution of 9.01 g of ethyl acrylate and 8.1 g of heptane was added dropwise. The obtained mixture was stirred at 70° C. for 1 hour, 20 mL of water was added, and then the obtained liquid was separated at 60° C. to give a solution containing 1-(4-chlorophenyl)pyrazolidin-3-one. The solution was concentrated to give a slurry. 6.9 g of concentrated hydrochloric acid was added to the slurry, and then an aqueous solution prepared by mixing 3.02 g of sodium nitrite and 8.1 g of water was added, followed by stirring for 1.5 hours. An aqueous solution containing 0.76 g of sodium nitrite was added and stirred for 30 minutes, then water and toluene were added, and the mixture was filtered. The obtained solid was washed with toluene and then hexane, followed by drying to give 3.41 g of 4-chlorophenyl-1H-pyrazol-3-ol (content: 100 wt %). Yield: 78.4% (based on 4-chlorophenylhydrazine hydrochloride).

Example 7

60.00 g of 4-chlorophenylhydrazine hydrochloride, 300 g of toluene, and 200.42 g of a 28 wt % sodium methoxide/methanol solution were mixed and heated to 70° C. under a nitrogen atmosphere. Subsequently, 100.47 g of ethyl acrylate was added dropwise and stirred at 70° C. for 4 hours to give a mixture containing 1-(4-chlorophenyl)pyrazolidin-3-one. 60 g of water was added to the mixture and concentrated. 125.6 g of concentrated hydrochloric acid was added to the concentrated residue, and further 138.7 g of a 33 wt % aqueous sodium nitrite solution was added, followed by stirring at 5° C. for 2 hours. 120 g of water was added to the obtained reaction mixture and filtered, and the obtained solid was washed with water and then toluene, followed by drying to give 51.1 g of 4-chlorophenyl-1H-pyrazol-3-ol (content: 98.9 wt %). Yield: 78.2% (based on 4-chlorophenylhydrazine hydrochloride).

INDUSTRIAL APPLICABILITY

According to the present invention, a pyrazole compound useful as an intermediate in the production of pharmaceuticals, etc., can be industrially produced.

The invention claimed is:

1. A method for producing a pyrazole compound represented by formula (1):

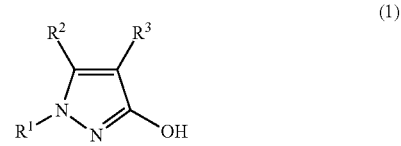

(wherein $R^1$ represents an optionally substituted $C_{1-12}$ alkyl group, an optionally substituted $C_{3-12}$ cycloalkyl group, an optionally substituted $C_{6-16}$ aryl group, or an optionally substituted pyridyl group, $R^2$ and $R^3$ each independently represent a hydrogen atom, a halogen atom, a $C_{1-3}$ alkyl group, or a $C_{1-3}$ haloalkyl group), comprising a step of allowing a pyrazolidine compound represented by formula (2):

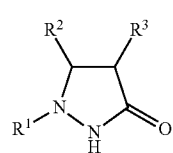

(2)

(wherein $R^1$, $R^2$, and $R^3$ are as defined above)

to react with a nitrite in the presence of an acid.

2. The method according to claim 1, wherein $R^2$ and $R^3$ are both hydrogen atoms.

3. The method according to claim 1, wherein $R^1$ is an optionally substituted $C_{6-16}$ aryl group optionally substituted with at least one substituent selected from the following group P or a pyridyl group optionally substituted with at least one substituent selected from the following group Q:

Group P: a halogen atom, a $C_{1-6}$ alkoxy group, a $C_{1-6}$ haloalkyl group, a $C_{1-6}$ haloalkoxy group, a nitro group, and a cyano group;

Group Q: a $C_{1-6}$ alkyl group, a halogen atom, a $C_{1-6}$ alkoxy group, a $C_{1-6}$ haloalkyl group, a $C_{1-6}$ haloalkoxy group, a nitro group, and a cyano group.

4. The method according to claim 1, wherein $R^1$ is a 4-chlorophenyl group, and $R^2$ and $R^3$ are both hydrogen atoms.

5. The method according to claim 1, further comprising a step of allowing a hydrazine compound represented by formula (3):

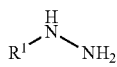

(3)

(wherein $R^1$ represents an optionally substituted $C_{1-12}$ alkyl group, an optionally substituted $C_{3-12}$ cycloalkyl group, an optionally substituted $C_{6-16}$ aryl group, or an optionally substituted pyridyl group)

to react with a compound represented by formula (4):

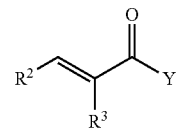

(4)

(wherein Y represents a $C_{1-4}$ alkoxy group, and $R^2$ and $R^3$ each independently represent a hydrogen atom, a halogen atom, a $C_{1-3}$ alkyl group, or a $C_{1-3}$ haloalkyl group)

in the presence of a base, thereby giving a pyrazolidine compound represented by formula (2).

6. The method according to claim 5, wherein $R^2$ and $R^3$ are both hydrogen atoms.

7. The method according to claim 5, wherein $R^1$ is an optionally substituted $C_{6-16}$ aryl group optionally substituted with at least one substituent selected from the following group P or a pyridyl group optionally substituted with at least one substituent selected from the following group Q:

Group P: a halogen atom, a $C_{1-6}$ alkoxy group, a $C_{1-6}$ haloalkyl group, a $C_{1-6}$ haloalkoxy group, a nitro group, and a cyano group;

Group Q: a $C_{1-6}$ alkyl group, a halogen atom, a $C_{1-6}$ alkoxy group, a $C_{1-6}$ haloalkyl group, a $C_{1-6}$ haloalkoxy group, a nitro group, and a cyano group.

8. The method according to claim 5, wherein $R^1$ is a 4-chlorophenyl group, and $R^2$ and $R^3$ are both hydrogen atoms.

* * * * *